(12) United States Patent  
Endo et al.

(10) Patent No.: US 8,414,125 B2  
(45) Date of Patent: Apr. 9, 2013

(54) APPARATUS FOR MEASURING DISTANCE BETWEEN EYE TISSUES

(75) Inventors: Masakazu Endo, Aichi (JP); Noriji Kawai, Aichi (JP); Yasuhisa Murakami, Aichi (JP)

(73) Assignee: Nidek Co., Ltd., Aichi (JP)

( * ) Notice: Subject to any disclaimer, the term of this patent is extended or adjusted under 35 U.S.C. 154(b) by 239 days.

(21) Appl. No.: 12/958,552

(22) Filed: Dec. 2, 2010

(65) Prior Publication Data

US 2011/0128499 A1  Jun. 2, 2011

(30) Foreign Application Priority Data

Dec. 2, 2009 (JP) ................................. 2009-274060

(51) Int. Cl.  
*A61B 3/10* (2006.01)

(52) U.S. Cl.  
USPC ........................................................ 351/221

(58) Field of Classification Search .................. 351/221, 351/212, 208, 209, 246, 205; 600/398, 475, 600/427  
See application file for complete search history.

(56) References Cited

U.S. PATENT DOCUMENTS

| 6,779,891 | B1 | 8/2004 | Barth et al. |
| 2007/0282313 | A1 | 12/2007 | Huang et al. |
| 2010/0201946 | A1 | 8/2010 | Murakaimi |
| 2011/0228218 | A1* | 9/2011 | Hauger et al. ............... 351/205 |

FOREIGN PATENT DOCUMENTS

| JP | 2002531205 | 9/2002 |
| JP | 2005160694 | 6/2005 |
| JP | 2010184049 | 8/2010 |

OTHER PUBLICATIONS

Extended European Search Report for 10193096.4-2319 dated Nov. 21, 2011.

* cited by examiner

*Primary Examiner* — Hung Dang  
(74) *Attorney, Agent, or Firm* — Lowe Hauptman Ham & Berner, LLP

(57) ABSTRACT

An eye distance measurement apparatus according to one aspect of the invention includes an interfering optical system that projects at least one piece of split light toward an examinee's eye, combines the split light, guides the combined light to a light receiving device and moves an optical member in order to adjust an optical path difference between the two pieces of split light, a mode switching unit that issues a mode switching signal for switching between a first measurement mode for moving the optical member at a first scanning rate and a second measurement mode for moving the optical member at a second scanning rate slower than the first scanning rate, and a calculation and control unit that measures an eye distance, based on an output signal of the light receiving device, obtained in the measurement mode corresponding to the mode switching signal.

12 Claims, 2 Drawing Sheets

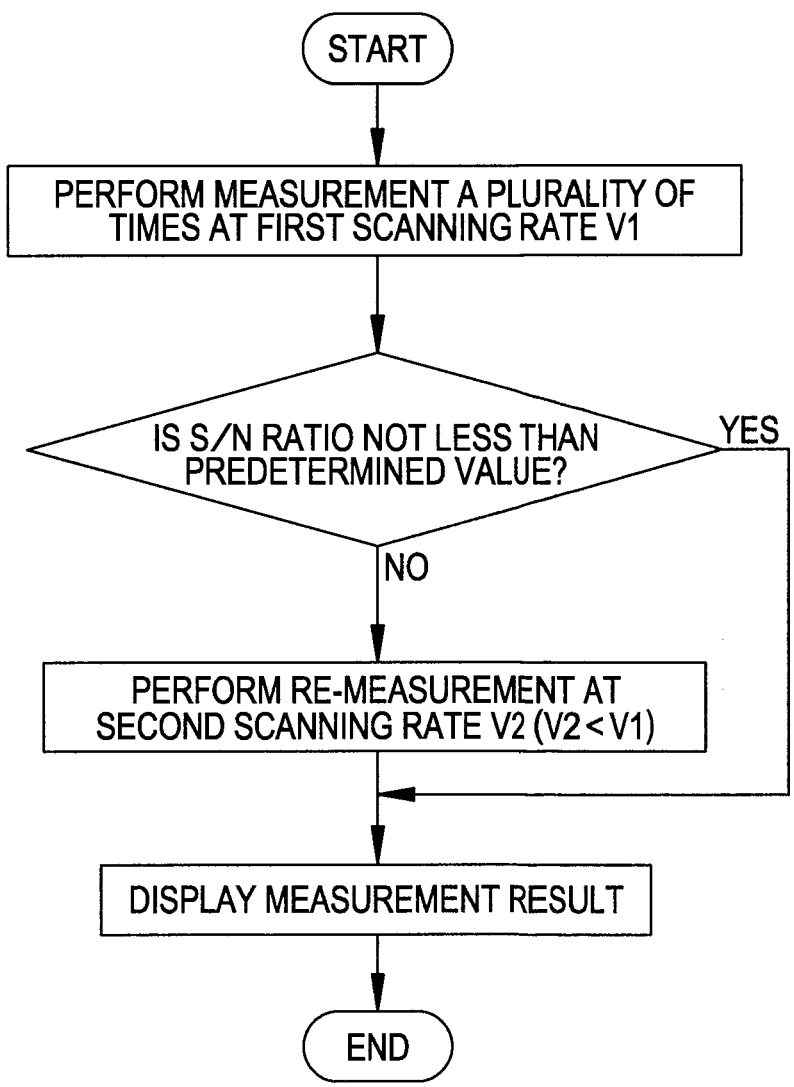

APPARATUS FOR MEASURING DISTANCE BETWEEN EYE TISSUES

CROSS-REFERENCE TO RELAYED APPLICATION

This application is based on Japanese Patent Application No. 2009-274060 filed with the Japan Patent Office on Dec. 2, 2009, the entire content of which is hereby incorporated by reference.

BACKGROUND

1. Technical Field

The present invention relates to an apparatus for measuring a distance between eye tissues which measures a distance between tissues of an examinee's eye.

2. Related Art

An apparatus for measuring a distance between eye tissues projects measurement light toward an examinee's eye and detects the reflected light with a light receiving device as interference light to measure an axial distance between eye tissues (e.g., ocular axial length, anterior chamber depth) (e.g., refer to Patent Document 1).

Documents that describe the related art are listed below.
Patent Document 1: JP 2002-531205 A (PCT)
Patent Document 2: JP 2005-160694 A However, in the case of measuring a severe cataract eye with the conventional apparatus, little light has been returned from a fundus. This has caused insufficient obtainment of an S/N ratio of an interference signal, thus making distance measurement difficult.

SUMMARY

In view of the above problem, a technical object of the present invention is to provide an apparatus for measuring a distance between eye tissues which is capable of improving the accuracy in measurement on a severe cataract eye and smoothly performing the measurement.

To solve the above problem, the present invention has the following configuration.

An apparatus for measuring a distance between eye tissues includes an interfering optical system, a mode switching unit, and a calculation and control unit. The interfering optical system includes a light source, a beam splitter for splitting light emitted from the light source into first split light and second split light, an emitting optical system for projecting at least one of the first split light and the second split light toward an examinee's eye, a light receiving optical system for combining the two pieces of split light including the split light reflected by the examinee's eye and guiding the combined light to a light receiving device, and a driving part for moving an optical member in order to adjust an optical path difference between the first split light and the second split light. The mode switching unit issues a mode switching signal for switching a measurement mode between at least two measurement modes including a first measurement mode for measuring a distance between tissues of the examinee's eye while moving the optical member at a first scanning rate, and a second measurement mode for measuring a distance between the tissues of the examinee's eye while moving the optical member at a second scanning rate which is slower than the first scanning rate. The calculation and control unit performs operations of changing a scanning rate of the optical member at the time of measurement in accordance with the mode switching signal issued by the mode switching unit, controlling an operation of the driving part such that the optical member is moved at a scanning rate corresponding to the measurement mode switched by the mode switching unit, and measuring a distance between the tissues of the examinee's eye, based on an output signal of the light receiving device, obtained at the time of moving the optical member.

According to the present invention, it is possible to improve the accuracy in measurement on a severe cataract eye, and also to smoothly perform the measurement.

BRIEF DESCRIPTION OF THE DRAWINGS

The foregoing and other objects, features, aspects and advantages of the invention will become more apparent from the following detailed description when taken in conjunction with the accompanying drawings, in which:

FIG. 2 is a flowchart for illustrating an operation of the apparatus according to the present embodiment.

DESCRIPTION OF EMBODIMENTS

Figure 1:
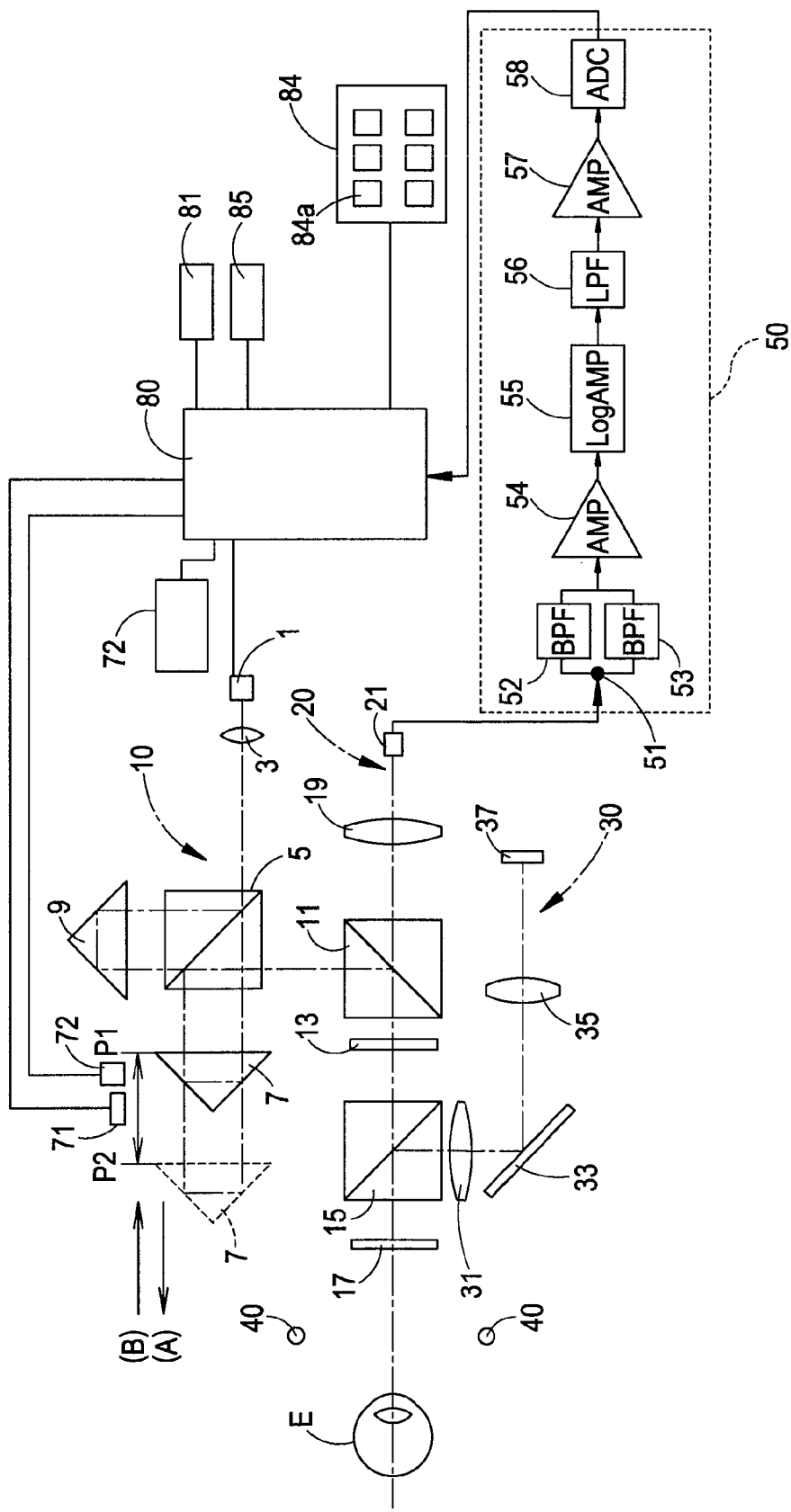
FIG. 1 is a view illustrating a schematic configuration of an optical system and a control system in an apparatus for measuring a distance between eye tissues according to one embodiment of the present invention.

Preferred embodiments of the present invention will be described below with reference to the accompanying drawings, in which like reference characters designate similar or identical parts throughout the several views thereof.

FIG. 1 is a view illustrating a schematic configuration of an optical system in an apparatus for measuring a distance between eye tissues according to one embodiment of the present invention. It is to be noted that the following embodiment is described taking an apparatus for measuring an ocular axial length as an example.

An emitting optical system 10 includes a measurement light source 1, a collimator lens 3, a beam splitter 5, a first triangular prism (corner cube) 7, a second triangular prism 9, a polarization beam splitter 11, a quarter wavelength plate 13, and an examination window 17. The measurement light source 1 is a light source that emits low coherent light (e.g., SLD (Super Luminescent Diode)). The collimator lens 3 collimates the light flux emitted from the light source 1 into parallel light flux. The beam splitter 5 splits the light emitted from the light source 1. The first triangular prism 7 is disposed in a transmitting direction of the beam splitter 5. The second triangular prism 9 is disposed in a reflecting direction of the beam splitter 5. The emitting optical system 10 is disposed so as to project (transmit) measurement light onto a cornea and a fundus of an examinee's eye.

The light (linearly polarized light) emitted from the light source 1 is collimated by the collimator lens 3, and then split into first measurement light (reference light) and second measurement light by the beam splitter 5. The first measurement light is reflected and returned by the triangular prism 7. Meanwhile, the second measurement light is reflected and returned by the triangular prism 9. Thereafter, the first measurement light and second measurement light are combined by the beam splitter 5. The combined light is reflected by the polarization beam splitter 11, and then converted into circularly polarized light by the quarter wavelength plate 13. This circularly polarized light is then projected onto at least the cornea and the fundus via a dichroic mirror 15 and the examination window 17. At this time, when measured light flux made up of this circularly polarized light is reflected by the cornea and the fundus, a phase of this light flux is displaced by a ½ wavelength.

A light receiving optical system 20 includes the examination window 17, the quarter wavelength plate 13, the polarization beam splitter 11, a condenser lens 19, and a light receiving device 21. The light receiving optical system 20 is disposed for receiving light (interference light) obtained by interference of reflected light obtained by reflection of measurement light on the cornea with reflected light obtained by reflection of measurement light on the fundus.

Herein, the cornea reflected light and the fundus reflected light travel via the examination window 17 and the dichroic mirror 15, and are converted into linearly polarized light by the quarter wavelength plate 13. Then, both the pieces of reflected light transmitted through the polarization beam splitter 11 are collected by the condenser lens 19, and received by the light receiving device 21.

It is to be noted that the triangular prism 7 is used as an optical-path-length changing optical member (optical-path-length changing member) for changing an optical path length. By driving of the driving part 71 (e.g., motor), the triangular prism 7 is linearly moved with respect to the beam splitter 5 along an optical axis direction. In addition, the scanning rate (movement rate) of the prism 7 at the time of measurement is changed by switching a measurement mode (to be described later) in each measurement. This optical-path-length changing optical member may be a triangular mirror. Further, a position of the prism 7 at the time of driving is detected by a position detection sensor 72 (e.g., potentiometer, encoder).

It should be noted that the foregoing optical-path-length changing optical member should be disposed on any of a plurality of measurement optical paths obtained by splitting by an optical path splitting member. The optical-path-length changing optical member may be moved so as to adjust an optical path difference between the plurality of measurement optical paths. For example, the optical-path-length changing optical member and the optical path splitting member may be disposed on an optical path of the emitting optical system 10 as in FIG. 1, may be disposed on an optical path of the light receiving optical system 20, or may be disposed on a common optical path of the emitting optical system 10 and the light receiving optical system 20.

An anterior segment imaging optical system 30 disposed for capturing an image of an anterior segment of the eye is provided in a reflecting direction of the dichroic mirror 15. The imaging optical system 30 includes the dichroic mirror 15, an objective lens 31, a total reflection mirror 33, an image forming lens 35, and a two-dimensional imaging device 37. The dichroic mirror 15 has a characteristic of transmitting light emitted from the light source 1, while reflecting light (e.g., infrared light) emitted from a light source 40 for illuminating the anterior segment. Herein, an anterior segment image, obtained by illumination by the illumination light source 40, is formed on the two-dimensional imaging device 37 via the examination window 17, the dichroic mirror 15, the objective lens 31, the total reflection mirror 33 and the image forming lens 35.

Next, a description is given to a control system of the apparatus according to the present embodiment. A control part 80 is connected with a display monitor 81, the light source 1, the light receiving device 21, a driving part 71, a position detection sensor 72, a control part 84, a memory 85, a signal processing part 50, and the like. The control part 80 obtains an ocular axial distance by calculation, using an interference signal output from the light receiving device 21. Further, the obtained measurement value and the like are stored in the memory 85. Moreover, the control part 84 is provided with a variety of switches such as a measurement start switch 84a to emit a trigger signal for starting measurement.

Further, the apparatus for measuring a distance between eye tissues according to the present embodiment has a first measurement mode and a second measurement mode. In the first measurement mode, an ocular axial length is measured while the prism 7 is moved at a first scanning rate V1 in accordance with a mild cataract eye. In the second measurement mode, an ocular axial length is measured while the prism 7 is moved at a second scanning rate V2 in accordance with a severe cataract eye. It is to be noted that the first scanning rate V1 and the second scanning rate V2 have a relation of V1>V2.

When a mode switching signal is issued automatically or manually, the control part 80 changes the scanning rate of the prism 7 at the time of measurement in accordance with the mode switching signal. The control part 80 then controls driving of the driving part 71 such that the prism 7 is moved at the scanning rate corresponding to the set measurement mode.

It should be noted that the second measurement mode is provided for measuring an eye which is not suitably measurable on the first measurement mode. Such an eye is, for example, an eye with which an acceptable S/N ratio of the interference signal cannot be obtained. In addition, a distinction between mild cataract and severe cataract is normally made by stage of cataract progression. However, in the following description, the distinction is made based on whether or not the S/N ratio of the interference signal exceeds a predetermined acceptable value at the time of measurement on the first measurement mode.

Further, the S/N ratio (SNR: Signal to Noise Ratio) of the interference signal is an amount of noise with respect to the interference signal, and expressed using logarithm. Generally, the higher the S/N ratio value, the higher quality signal with smaller noise can be obtained. Also in the present embodiment, the higher the S/N ratio, the more highly sensitive interference signal can be obtained.

The control part 80 has a signal processing part 50 for processing a light receiving signal output from the light receiving device 21. The signal processing part 50 is provided with a circuit switching part 51, a first band-pass filter 52, a second band-pass filter 53, an amplifier 54, a nonlinear amplifier (log amplifier) 55, a low-pass filter 56, an amplifier 57, and an A/D converter 58. The first band-pass filter 52 and the second band-pass filter 53 are switched in accordance with the measurement mode such that either mode is used. The A/D converter 58 converts an analog light receiving signal output from the amplifier 57 into a digital signal. It is to be noted that each member provided in the signal processing part 50 can be formed using a variety of electric circuits (e.g., FPGA).

The circuit switching part 51 switches connection of the two band-pass filters. The first band-pass filter 52 and the second band-pass filter 53 are members for extracting a beat signal (beat component) from a signal output from the light receiving device 21. The beat signal is a signal in a predetermined frequency band (beat frequency band) with a beat frequency regarded as a reference. That is, these filters 52 and 53 allow passage therethrough of the beat signal, while removing the other signals in the other frequency bands. A beat frequency νd is expressed as: νd=2V/λc, in which V represents a movement rate of the prism 7 and λc represents a center wavelength of the light source 1.

It should be noted that, when the movement rate of the prism 7 is switched, the beat frequency band changes. Therefore, the filter 52 is set so as to extract a beat signal in the case of the prism 7 being moved at the first scanning rate V1. Meanwhile, the filter 53 is set so as to extract a beat signal in the case of the prism 7 being moved at the second scanning rate V2. The control part 80 then switches the band-pass filter to be used in accordance with the mode switching signal. Thus, the control part 80 changes the beat frequency band, i.e., the frequency band for extracting an interference signal from a light receiving signal.

The nonlinear amplifier 55 is a member (envelope detection circuit) for obtaining and outputting an envelope of a beat signal amplified by the amplifier 54.

The low-pass filter 56 is a member for extracting an interference light component (interference signal) from an output signal (envelope signal) output from the nonlinear amplifier 55. The low-pass filter 56 allows passage therethrough of a signal with a frequency not more than a predetermined frequency among envelope signals output from the nonlinear amplifier 55, while cutting off a signal with a frequency exceeding the predetermined frequency. The signal with a frequency not more than the predetermined frequency corresponds to the envelope based on the interference signal.

A description is given to the case of measuring an ocular axial length with the apparatus having such a configuration as above. The examiner moves the apparatus in up-to-down, right-to-left and back-to-forth directions by use of an operating means such as a joystick, not illustrated, while observing an alignment state of the eye which is displayed on the monitor 81. The examiner then places the apparatus at a predetermined position with respect to an eye E. In this case, the examiner instructs the eye E be fixated to a fixation target, not illustrated.

FIG. 2 is a flowchart for illustrating an operation of the apparatus according to the present embodiment. At the initial stage, the first measurement mode is set. In this case, the first band-pass filter 52 is used by the circuit switching part 51.

When a trigger signal for starting measurement is output automatically or manually, the measurement light source 1 is lighted by the control part 80. Thus, measurement light is projected onto the eye E by the emitting optical system 10. Then, reflected light obtained by reflection of the measurement light on the eye E is incident on the light receiving device 21 of the light receiving optical system 20.

Further, the control part 80 controls driving of the driving part 71, to reciprocate the first triangular prism 7 at the first scanning rate V1. The control part 80 then calculates an ocular axial length, based on the timing at which interference light is detected by the light receiving device 21.

The first scanning rate V1 is set to such a rate that the S/N ratio of the interference signal satisfies a predetermined acceptable value when a normal eye and mild cataract is measured. The rate is calculated by a predetermined calculating expression and/or experiment, and the like. For example, the rate is set to a rate to such a degree that the prism 7 can move in a movable range (P1 to P2), corresponding to a predetermined measurable range, in about 0.5 seconds.

In the case of the reciprocation, the control part 80 obtains a first interference signal output from the light receiving device 21 at the time of the first triangular prism 7 being moved in a first direction (direction A). The control part 80 then obtains a second interference signal output from the light receiving device 21 at the time of the first triangular prism 7 being moved in a second direction (direction B) that is reverse to the first direction. The control part 80 respectively measures an ocular axial length based on the first interference signal and an ocular axial length based on the second interference signal.

The position of the prism 7 in movement at the time of the interference signals being output from the light receiving device 21 varies in accordance with the ocular axial length. The position can be detected based on signals output from the position detection sensor 72. The position is thus detectable based on a signal output from a position detection sensor 72. Accordingly, it is for example preferable to previously obtain a relation between the position of the prism 7 and the ocular axial length by use of a predetermined arithmetic expression, a table, or the like. It is thereby possible to calculate an ocular axial length value based on the position of the prism 7 at the time of the interference signal being output.

The control part 80 acquires the first interference signal when the prism 7 is moved in the direction A. The control part 80 obtains a first measurement result on the ocular axial length, based on the position of the prism 7 when the first interference signal is acquired. The control part 80 then acquires the second interference signal when the prism 7 is moved in the direction B. The control part 80 obtains a second measurement result on the ocular axial length, based on the position of the prism 7 when the second interference signal is acquired. Thus, the ocular axial length is measured twice during one time of reciprocation of the prism 7. Accordingly, it is possible to smoothly perform continuous measurement.

The obtained information on the ocular axial length (measurement result) is stored in the memory 85. Further, after completion of a predetermined number of times of measurement (or after obtainment of a predetermined number of values of the examinee's ocular axial length), the control part 80 completes the reciprocation of the prism 7, and returns the prism 7 from the moving position to the initial position.

After completion of the measurement on the first measurement mode as described above, the control part 80 determines whether or not the S/N ratio of the interference signal is not less than the predetermined value. It is to be noted that this determination may be made on an S/N ratio of the light receiving signal. Further, in that case, the light receiving signal at a stage before extraction of the interference signal may be used. When the S/N ratio is not less than the predetermined value, the control part 80 displays the measurement result on the first measurement mode on the monitor 81, and then completes the measurement.

On the other hand, when the S/N ratio falls below the predetermined value, the control part 80 automatically issues a mode switching signal to switch the measurement mode from the first measurement mode to the second measurement mode. The control part 80 then performs re-measurement on the ocular axial length. Herein, the control part 80 transmits a switching signal to the circuit switching part 51, and switches the band-pass filter to be used to the second band-pass filter corresponding to the second scanning rate V2. It should be noted that at this time, the control part 80 may display the measurement result, the S/N ratio and the like on the first measurement mode on the monitor 81.

When a trigger signal for starting measurement is issued automatically or manually, the control part 80 controls driving of the driving part 71 to move (or reciprocate) the first triangular prism 7 at the second scanning rate V2. The control part 80 then calculates an ocular axial length, based on the timing at which the interference light is detected by the light receiving device 21.

The second scanning rate is set to a rate slower than the first scanning rate, such that the S/N ratio of the interference signal satisfies a predetermined acceptable value at the time of measurement on the severe cataract eye. The rate is preferably a rate to such a degree that the prism 7 can scan a predetermined movable range (P1 to P2) at least once within the time (within about three seconds) when stable fixation of the eye is sustainable. After obtainment of a result of measurement on the ocular axial length on the second measurement mode, the control part 80 displays this result of the re-measurement on the monitor 81.

Hereinafter, the relation between the scanning rate and the S/N ratio of the optical-path-length changing optical member is specifically described. Herein, the first scanning rate on the first measurement mode is taken as V1 (m/s). The second scanning rate on the second measurement mode is taken as V2 (m/s). In this case, the relation between the S/N ratio (SNR) and the scanning rate can be expressed by the following mathematical expressions (1) and (2).

$$SNR = \frac{\eta \cdot P_{sample}}{E_v \cdot BW} \quad (1)$$

$$BW = 2 \cdot \Delta f = 2 \cdot \left(\frac{2v}{\lambda_{min}} - \frac{2v}{\lambda_{max}}\right) = 4v \frac{\lambda_{max} - \lambda_{min}}{\lambda_{max} \cdot \lambda_{min}} \cong \frac{4v\Delta\lambda}{\lambda_0^2} \quad (2)$$

Herein, η represents a light receiving efficiency (including the optical system and the light receiving device), $P_{sample}$ represents a light receiving amount on the object light side, $E_v$ represents light energy, BW represents a width of a frequency band (beat frequency band) used for signal detection, ν represents a scanning rate, $\lambda_0$ represents a center wavelength of the light source, and Δλ represents a spectrum width. For example, when $\lambda_0$=830 nm and Δλ=8 nm, the scanning rate is preferably set between 10 mm/s and 400 mm/s, approximately.

In this case, with decrease in ν, BW decreases while the S/N ratio increases. In other words, when the scanning rate of the prism 7 becomes slower, ν decreases, and the S/N ratio thus increases. As a result, the sensitivity of the interference signal increases. Specifically, by measurement at the second scanning rate V2 which is slower than the first scanning rate V1 (V2<V1), the measurement time becomes longer, but the S/N ratio becomes higher than in the measurement at the first scanning rate V1. Therefore, even in a case where a large portion of measurement light is shielded inside the eye to make a light amount level of the interference light small, as in the case of implementing measurement on the eye suffering from severe cataract, an S/N ratio acceptable to a certain degree can be ensured.

In the apparatus having the foregoing configuration, measurement is implemented at the second scanning rate V2 on the eye with high degree of difficulty in measurement, such as the severe cataract eye. Thus, the sensitivity of the interference signal increases, and the acceptable measurement accuracy can be obtained. Further, in this apparatus, measurement can be implemented on the first measurement mode as the initial setting on the normal eye or the mild cataract eye. It is therefore possible to smoothly implement measurement by use of the first scanning rate V1.

In the apparatus, in order to automatically issue the switching signal for switch to the second measurement mode, a configuration may be employed where a light receiving part (light receiving device) is provided which receives reflected light obtained by reflection of measurement light on a tissue (e.g., fundus) of the examinee's eye, and a switching signal for switch of the measurement mode to the second measurement mode is issued based on a light receiving signal output form the light receiving part. For example, the control part 80 may determine whether or not a light amount of the light receiving signal exceeds a predetermined threshold, and may issue a switching signal depending on a determination result.

It is to be noted that the light receiving part is not limited to the light receiving device 21. For example, the light receiving part may be a member that captures an image inside the pupil, formed by fundus reflected light, on the imaging device 37 and determines by image processing the presence or absence of opacity due to the cataract.

It is to be noted that in the present embodiment, the configuration of automatically switching the mode is described. However, the apparatus may be configured to be provided with a mode selection switch to be operated by the examiner. In this configuration, for example, the examiner checks the S/N ratio, and operates the mode selection switch, based on a result of the checking. Then, the measurement mode is switched based on an operation signal from this switch.

It is to be noted that in the foregoing description, signals are processed using hardware (circuit configuration) such as the signal processing part 50. However, this is not restrictive, and similar signal processing may be performed by use of arithmetic processing by software. For example, the control part 80 performs Fourier analysis on a light receiving signal I(t) output from the light receiving device 21 to acquire a frequency spectrum I(f). The control part 80 then detects a beat frequency νd by use of the acquired frequency spectrum I(f). Based on the detected beat frequency νd, the control part 80 changes a frequency band for extracting an interference signal from a light receiving signal by use of a band-pass filter constructed by software. Thus, in a light receiving signal I(t) output from the light receiving device 21, a light receiving signal in a frequency band with the beat frequency Vd taken at the center is extracted as an interference signal. Thereafter, the control part 80 measures an ocular axial length by use of the extracted interference signal. In this case, the first band-pass filter that extracts a beat signal corresponding to the first measurement mode and the second band-pass filter that extracts a beat signal corresponding to the second measurement mode are formed by software.

It is to be noted that in measurement on a patient having normal eyes, an S/N ratio not less than a predetermined value may be obtained even when the scanning rate is made faster than the first scanning rate. Therefore, not only the second scanning rate mode, but a third measurement mode on which the scanning rate of the prism 7 is made faster than the first measurement mode may be provided. In this case, a band-pass filter corresponding thereto is provided. In such a manner, measurement on the normal eye can be completed in a shorter period of time. This can alleviate load of the patient. In this case, the first measurement mode is a mode dealing with mild cataract.

It is to be noted that in the present embodiment, the configuration is described where the scanning rate can be switched in two stages by switching the measurement mode. However, this configuration is not necessarily employed. The apparatus for measuring a distance between eye tissues may be configured such that three or more measurement modes can be set. For example, this apparatus may be configured such that a member, with which an arbitrary scanning rate can be input by the examiner in a predetermined range, can be provided and measurement can be performed at the input scanning rate. The examiner can thereby perform more delicate adjustment.

Further, in the present embodiment, the configuration is described where the cornea reflected light and the fundus reflected light are interfered with each other. However, this configuration is not necessarily employed. For example, the apparatus for measuring a distance between eye tissues according to the present invention may be an apparatus for measuring a distance between eye tissues, provided with a light interfering optical system including a beam splitter (light splitting member) that splits light emitted from the light source, a sample arm that forms an object optical path, a reference arm that forms a reference optical path, and a light receiving device for receiving interference light. In this light interfering optical system, interference light obtained by interference of measurement light projected onto the eye via the sample arm with reference light from the reference arm is received by the light receiving device. In this case, the optical-path-length changing optical member is provided in at least one of the sample arm and the reference arm.

Moreover, in the present embodiment, the configuration is described where the prism 9 is linearly moved to change an optical path length of reference light. However, this configuration is not necessarily employed. For example, the apparatus for measuring a distance between eye tissues according to the present invention may be configured to change an optical path length of reference light by a light delaying mechanism to move a rotary reflector (e.g., refer to JP 2005-160694 A). In this case, a movement rate of the rotary reflector is changed in accordance with the first measurement mode and the second measurement mode.

Alternatively, the apparatus for measuring a distance between eye tissues according to the embodiment of the present invention may be configured as an eye distance measurement apparatus for measuring an eye distance corresponding to a distance between tissues of an examinee's eye using interference light obtained by interference between a plurality of pieces of measurement light including measurement light reflected from the examinee's eye, the plurality of pieces of measurement light being different in optical path length from one another. This eye distance measurement apparatus may include an optical member that moves on one of the optical paths of the measurement light to adjust an optical path difference between the plurality of pieces of measurement light, and a control unit that measures the eye distance, based on a position of the optical member where the interference light appears. Herein, the control unit may be set to change a movement rate of the optical member to adjust intensity of the interference light.

While the invention has been illustrated and described in detail, the foregoing description is in all aspects illustrative and not restrictive. It is therefore understood that numerous modifications and variations can be devised without departing from the spirit and scope of the invention.

What is claimed is:

1. An apparatus for measuring an ocular axial length, the apparatus comprising:
    an interfering optical system that includes
        an emitting optical system including
            a light source configured to emit light, and
            a beam splitter for splitting the light emitted from the light source into first split light and second split light, wherein the emitting optical system is configured to project at least one of the first split light and the second split light toward an examinee's eye,
        a light receiving optical system configured to
            receive interference light obtained by an interference of the first split light and the second split light reflected at the examinee's eye, and
            output an interference signal, and
        an optical member configured to adjust an optical path difference between the first split light and the second split light and disposed on at least one of an optical path of the emitting optical system or an optical path of the light receiving optical system, and
    a driving part configured to move the optical member;
    a mode switching unit configured to issue a mode switching signal for switching a measurement mode between at least two measurement modes including
        a first measurement mode for measuring the ocular axial length while moving the optical member at a first scanning rate, and
        a second measurement mode for measuring the ocular axial length while moving the optical member at a second scanning rate slower than the first scanning rate; and
    a calculation and control unit configured to
        change a scanning rate of the optical member based on the mode switching signal issued by the mode switching unit,
        control an operation of the driving part to move the optical member at the scanning rate corresponding to the measurement mode switched by the mode switching unit, and
        measure the ocular axial length based on the interference signal output from the light receiving optical system.

2. The apparatus according to claim 1, wherein
the light receiving optical system includes a light receiving device configured to receive the interference light and output the interference signal, and
the mode switching unit is configured to automatically issue a mode switching signal for switching to the second measurement mode, based on the interference signal output from the light receiving device.

3. The apparatus according to claim 2, wherein
when a signal-to-noise (S/N) ratio of the interference signal output from the light receiving device is not less than a predetermined value at a time of measurement in the first measurement mode, the mode switching unit is configured to end the measurement, and
when the S/N ratio of the interference signal output from the light receiving device is below the predetermined value at the time of measurement in the first measurement mode, the mode switching unit is configured to automatically issue the mode switching signal for switching the measurement mode from the first measurement mode to the second measurement mode.

4. The apparatus according to claim 2, wherein
the calculation and control unit includes
    a first band-pass filter for extracting a beat signal corresponding to the first measurement mode, from the interference signal output from the light receiving device, and
    a second band-pass filter for extracting a beat signal corresponding to the second measurement mode, from the interference signal output from the light receiving device, and
the calculation and control unit is further configured to change a frequency band of the beat signal extracted from the interference signal in accordance with the mode switching signal.

5. The apparatus according to claim 1, further comprising a mode selection switch for manually selecting the operation mode, wherein
the mode switching unit is configured to issue the mode switching signal, based on an operation signal output from the mode selection switch operated by an examiner.

6. The apparatus according to claim 1, wherein the mode switching unit is configured to issue a mode switching signal for switching the measurement mode among at least three or more measurement modes with mutually different scanning rates of the optical member.

7. The apparatus according to claim 1, wherein
the emitting optical system further includes a second optical member configured to reflect the second split light and is further configured to
combine the first split light reflected at the optical member and the second split light reflected at the second optical member to obtain measurement light, and
project the measurement light toward at least a corona and a fundus of the examinee's eye,
the light receiving optical system is further configured to receive interference light obtained by an interference of the measurement light reflected at the corona and the measurement light reflected at the fundus.

8. An ocular-axial-length measurement apparatus for measuring an ocular axial length using interference light obtained by an interference between a plurality of pieces of measurement light including measurement light reflected from the examinee's eye, the plurality of pieces of measurement light being different in optical path length from one another, the eye distance measurement apparatus comprising:
an optical member configured to move on at least one of optical paths of plurality of pieces of the measurement light to adjust an optical path difference between the plurality of pieces of measurement light; and
a control unit configured to measure the ocular axial length, based on a position of the optical member where the interference light appears, wherein
the control unit is configured to change a scanning rate of the optical member to adjust intensity of the interference light while measuring the ocular axial length.

9. The ocular-axial-length measurement apparatus according to claim 8, wherein the control unit is configured to
reduce the movement rate of the optical member, and measure the ocular axial length again when it is determined that the intensity of the interference light, which is obtained by moving the optical member at a first scanning rate, is smaller than a predetermined value.

10. The ocular-axial-length measurement apparatus according to claim 9, wherein the control unit is configured to move the optical member at one of the first scanning rate and a second scanning rate slower than the first scanning rate.

11. The ocular-axial-length measurement apparatus according to claim 8, wherein the control unit is configured to change the scanning rate of the optical member, based on an externally input switching signal.

12. An eye distance measurement apparatus for measuring an eye distance corresponding to a distance between tissues of an examinee's eye using interference light obtained by interference between a plurality of pieces of measurement light including measurement light reflected at the examinee's eye, at least one of the plurality of pieces of measurement light being different in optical path length from one another, the eye distance measurement apparatus comprising:
an optical member configured to move on at least one of the optical paths of the plurality of pieces of measurement light to adjust an optical path difference between the plurality of pieces of measurement light; and
a control unit configured to measure the eye distance, based on a position of the optical member where the interference light appears, wherein
the control unit is configured to
reduce a scanning rate of the optical member to a second scanning rate when it is determined that an intensity of the interference light obtained by moving the optical member at a first scanning rate, which is faster than the second scanning rate, is smaller than a predetermined value, and
measure the eye distance again at the second scanning rate.

* * * * *